US005661119A

United States Patent [19]
Hersh et al.

[11] Patent Number: 5,661,119
[45] Date of Patent: Aug. 26, 1997

[54] SKIN CLEANSING FORMULATIONS WITH TERPENE SOLVENTS AND CORN MEAL SCRUBBER

[75] Inventors: Leslie J. Hersh, Saginaw; Richard C. Wallace, Bay City, both of Mich.; Elizabeth A. Bowley, Ripley, United Kingdom

[73] Assignee: Sprintvest Corporation NV, Piscadera Bay, Netherlands Antilles

[21] Appl. No.: 537,737

[22] PCT Filed: Jan. 26, 1994

[86] PCT No.: PCT/US94/00443
§ 371 Date: Apr. 30, 1993
§ 102(e) Date: Apr. 30, 1993

[87] PCT Pub. No.: WO94/25001
PCT Pub. Date: Nov. 10, 1994

Related U.S. Application Data

[63] Continuation-in-part of Ser. No. 55,740, Apr. 30, 1993, abandoned.

[51] Int. Cl.$^6$ .................. C11D 3/14; C11D 3/18; C11D 3/43; C11D 17/00
[52] U.S. Cl. .................. 510/139; 510/159; 510/417; 510/418; 510/420; 510/421; 510/422; 510/462; 510/463; 510/470
[58] Field of Search .................. 510/139, 268, 510/249, 462, 463, 470, 157–159, 418, 420, 421, 422, 505, 506, 417

[56] References Cited

FOREIGN PATENT DOCUMENTS 60-108499  6/1985  Japan .

OTHER PUBLICATIONS

CA abstract accession No. 104:226761, for FR 2564104, Nov. 15, 1985 1997.
Derwent abstract accession No. 86–001530, for FR 2564104, Nov. 15, 1985 1997.

*Primary Examiner*—Ardith Hertzog
*Attorney, Agent, or Firm*—Lynn C. Schumacher; Hill & Schumacher; Dowell & Dowell

[57] ABSTRACT

There is disclosed various terpene based cleansing formulations for skin. The cleaning formulations include the ingredients of water in which there is dispersed a terpene, nonionic surfactants, corn meal scrubber and preservatives including antimicrobial and antioxidant agents. In one aspect of the invention the skin cleansing formulations include orange terpenes as the solvent. The nonionic surfactants present in the formulation provide stabilization of the terpene/water mixture, do not soften or otherwise attack the corn meal, and provide detergency for suspending the lifted soil.

18 Claims, No Drawings

SKIN CLEANSING FORMULATIONS WITH TERPENE SOLVENTS AND CORN MEAL SCRUBBER

This patent application is a continuation-in-part application of U.S. patent application Ser. No. 08/055,740 filed on Apr. 30, 1993, entitled TERPENE-BASED SKIN CLEANSING FORMULATIONS, which is now abandoned.

FIELD OF THE INVENTION

The present invention relates to terpene based skin cleansing formulations containing ground corn meal (maize) as a scrubber.

BACKGROUND OF THE INVENTION

Citrus terpenes including orange terpenes and d-limonene are safe, effective and naturally occurring organic solvents currently used as a fragrance additive in various soap products and perfumes, and as well as a flavour additive in foodstuffs and beverages. Because for example d-limonene is an effective organic solvent it is also utilized in household and industrial cleaning products and is a viable alternative to potentially dangerous chlorinated hydrocarbon solvents.

Skin cleansing solutions based on solvents having abrasive particles dispersed therethrough are well known. Several types of mineral abrasives included in these skin cleaning formulations include diatomaceous earth, pumice, aluminum oxide and silica to mention just a few. A drawback to the use of mineral based abrasives relates to the hardness and very sharp edges of the particles which can result in micro-cuts to a user's skin upon use thereby causing undue irritation and possibly infection.

Plastic scrubber particles are used in some cleaning formulations but many types of plastic are subject 30. to attack and softening in terpene solvents thereby rendering the scrubber ineffective. Further, plastic scrubbers are not biodegradable and hence pose an environmental problem.

It is therefore desirable to provide a terpene based skin cleansing formulation including an abrasive which provides a gentle scrubbing action and which is not attacked by the terpene or surfactant system.

SUMMARY OF THE INVENTION

The present invention provides cleansing formulations for the skin using a terpene as the organic solvent. In one aspect of the invention there is provided a cleansing formulation for application to the skin comprising in combination, water, a physiologically acceptable terpene present in the range from about 0.9% to about 40% by weight, a nonionic surfactant present in the range from about 4% to 20% by weight, the nonionic surfactant being the primary surfactant of the formulations a corn meal scrubber present in the range from about 3% to about 20%, and a preservative present in range from about 0.05% to about 2.35% by weight.

In another aspect of the invention there is provided a cleansing formulation for application to the skin, comprising water, a terpene present in the amount from about 0.9% to 40% by weight; corn meal scrubber present in the range from about 3% to about 20% by weight; nonionic surfactants present in the range from about 4% to about 20% by weight; and the nonionic surfactants being the primary surfactants of the formulations a preservative comprising an antimicrobial agent and an antioxidant present in the range from about 0.10% to about 1.3% by weight; and a thickening agent present in the range from about 0.30% to about 2.35% by weight.

DETAILED DESCRIPTION OF THE INVENTION

Ingredients

A general description of the ingredients of the skin cleansing formulations will first be given followed by a more detailed description of the component ranges and non-limiting example formulations.

Organic Solvent

D-limonene is a naturally occurring biodegradable solvent found in the oil of citrus peels of limes, lemons and oranges to mention just a few sources. D-limonene provides good solvent power and has a Kauri-Butanol (K-B) value of about 62.7 which is indicative of its high solvent strength. Odourless mineral spirits by comparison has a K-B value of about 26. Since d-limonene is a safe and effective organic solvent it is currently utilized in household and industrial cleaning products.

D-limonene is a member of the chemical class known as dipentenes. Dipentenes other than d-limonene which also exhibit exceptional solvent power are derived from pine trees. The dipentenes in turn are part of a more general class of chemicals called citrus terpenes which as a group is characterized by strong solvent power. Some cuts of orange oil are sold as "orange terpenes" and function in an identical manner to the d-limonene organic solvent used in many of the representative examples disclosed below. Citrus terpenes are also part of the terpene family which are used in the present invention Therefore, those skilled in the art will readily understand that terpenes other than d-limonene may be used as the organic solvent in the skin cleansing formulations of the present invention as long as they are physiologically acceptable.

Surfactants

D-limonene dissolves hydrocarbon based soils. However, while 100% d-limonene or a d-limonene/water mixture will slowly dissolve many hydrocarbon based soils, the soil will simply move around on the skin and not readily rinse off. Therefore, a viable skin cleansing formulation based on d-limonene or other terpenes preferably includes a detergent.

The skin cleansing formulations include detergents to disperse and suspend the lifted soil so that it can be effectively rinsed off the skin. The general class of non-ionic surfactants including alkyl phenol ethoxylates (e.g. ethoxylated nonyl phenols), ethoxylated alcohols (e.g. Neodols, Shell Oil Co.) amine oxides, amides (e.g. Cocamide DEA or alkanolamide based surfactants derived from palm kernal oil such as Palm Kernalamide DEA) or various combinations thereof are suitable detergents which may be used in the formulations of the present invention. A preferred detergent used in the present formulations is nonoxynol-10, an ethoxylated nonyl phenol (one trade-name is Union Carbide Tergitol NP-10).

In order to hold together and stabilize emulsions of the organic terpenes with the water, a coupling agent or solubilizer may be required. While solubilizers and coupling agents perform essentially the same function, the term coupling agent usually describes materials which produce a true solution. A preferred solubilizer used in many of the formulations is PEG-75 Lanolin. Other coupling agents or solubilizers which may be used in the present invention include hexylene glycol and Polyoxypropylene (24) Polyoxyethylene (24) Glyceryl Ether (PPG-24-Glycereth-24) sold by Dow Chemical Co. under the trade-name Polyglycol 15-200. This latter ingredient is used in cosmetic formulations as a solvent and solubilizer in lotions and creams. PPG-24-Glycereth-24 functions to stabilize the emulsification of the d-limonene and additionally provides the benefit of a water soluble solvent for organic hydrocarbon liquids. Further, PPG-24-Glycereth-24 may act as a lubricant to facilitate flow of certain formulations through dispensing systems. The formulations disclosed herein have been found to be quite stable with the solubilizer component present in the preferred range of from about 0.2% to about 3%.

Other ethers of glycerin which may be used as solubilizers include PPG-66-Glycereth-12 and PPG-20-Glycereth-30.

The solubilizer or coupling agent facilitates solubilization of the terpene in the primary surfactant. As such these are secondary surfactants which may not be necessary in all cleansing formulations falling within the ambit of the present invention.

Abrasive

The skin cleansing formulations of the present invention include ground corn meal to provide gentle scrubbing action. Corn in North America is referred to as maize in Europe and other countries. Corn meal as used herein is intended to cover a range of products derived from ground maize such as the endosperm, husk, cob and mixtures thereof. The corn meal aids in breaking up the mass of soil with itself as well as the bond between the soil and the skin much more rapidly than a composition comprising d-limonene without a scrubber. Corn meal is an advantageous scrubber in terpene based cleansing formulations because it is not characterized by sharp rigid edges and therefore will not produce micro-cuts on a user's skin during use as can occur with mineral abrasives. In addition, corn meal is biodegradable unlike most plastics and mineral scrubbers and therefore will not adversely impact on the environment.

The preferred particle size of the corn meal is chosen to provide a balance between obtaining a good cleaning or scrubbing action while at the same time avoiding problems of obstructing flow passageways in the dispensing mechanism being used to dispense the skin cleaning formulation. Particle sizes ranging from about 50 to 1000 microns and preferably 150 to about 250 microns have been found to satisfy these requirements.

Thickeners/Suspenders

In order to thicken the cleansing composition and to suspend the particulate, ground corn meal therein, a thickener/suspender may be utilized in some of the present formulations. Carbomer 940 is one member of a family of carbomers. Carbopol 940 is the BF Goodrich trade-name for carbomer 940 which is a cross-linked polymer of acrylic acid. This polymeric material may also act to enhance the suspension of the soil prior to rinse-off. This ingredient is also currently marketed in the United States by RITA Corporation under the trade-name Acritamer 940 (The manufacturer of the RITA material is Seitetsu Kagaku Co., Ltd. in Osaka, Japan). Carbomer 940 is an acid powder which is neutralized in the course of manufacture of the present formulations to provide a neutral thickening and suspension agent. Organics such as triethanolamine (TEA) and inorganic alkalis such as sodium hydroxide may be included in the present formulation to provide this neutralization. Carbomers 647 and 934 are two other non-limiting examples of carbomers which may be used as thickening agents in the formulations of the present invention.

While most carbomers are supplied as powders, some are sold dispersed in such vehicles as mineral spirits. Such a dispersed product may be used in the formulations disclosed herein. Some carbomers do not require neutralization.

Those skilled in the art will readily appreciate that powdered carbomers are difficult to effectively disperse in aqueous media prior to neutralization due to clumping whereby surface solvation prevents proper wetting of the interior of the clumps. If this clumping occurs, the product can become unacceptably lumpy.

There are three general methods which have been used for neutralizing the carbomers used in the formulations disclosed herein. One such method used in producing the formulations disclosed herein uses an eductor to disperse the powder rapidly in the water. Another method involves preparing a slurry of the carbomer suspended in the oily components of the mixture. A third method involves pro-blending the powdered carbomer with other powders to be included in the formulations, such as the corn meal abrasive component.

Details of these methods are described in the BF Goodrich information circular entitled "Carbopol® Water Soluble Resins" which is incorporated herein by reference.

Those skilled in the art will readily appreciate that other thickeners/suspenders may be used in the present invention and these may include other polymers and copolymers derived from acrylic acid. One alternative is the Rohm & Haas product Acrysol ICS-1 with the acrylate/steareth-20 methacrylate copolymer. This product is a water solution of the copolymer indicated. Polymers derived from cellulose gum may also be used thickening/suspending agents.

It will be understood by those skilled in the art that stable water/terpene formulations may be made without providing a specific thickening agent if the surfactant is chosen in such a way that the emulsified system is inherently thick enough to provide adequate suspension for the corn meal.

Preservatives

In order to prevent degradation and to extend the shelf life of the cleansing formulations, preservatives are included in the formulations to prevent deterioration due to potential microbial contamination or decomposition through oxidation with air. Examples of antimicrobial preservatives which may be used in the formulations include methylparaben, propylparaben, diazolidinyl urea (Trade-name Germall II, Sutton Chemical), and polymethoxy bicyclic oxazolidine (Trade-name Nuosept C, Huls America). For example, a commercial preservative blend which may be used in the present invention is sold under the tradename Germaben II by Sutton Chemical and is a solution of diazolidinyl urea, methylparaben and propylparaben in propylene glycol.

Alternative antimicrobial preservatives which may be used include other derivatives of para-hydroxybenzoic acid such as a blend of Isopropylparaben and isobutylparaben and butylparaben; 2-bromo-2-nitropropane-1,3-diol; methyldibromo glutaronitrile and phenoxyethanol. Other antimicrobial preservatives include formaldehyde, imadazolidinyl urea, quaternium-15, phenoxyethanol, chloroxylenol, DMDM Hydantoin, and a blend of methylchloroisothiazolinone and methylisothiazolinone.

Examples of anti-oxidant preservatives which may be used in the formulations of the present invention include butylated hydroxytoluene (BHT), butylated hydroxyanisole (BHA), sodium sulfite and tocopherol. Tocopheral is vitamin E which is an antioxidant and a natural source of tocopheral is wheat germ oil.

An antioxidant is sometimes added to the terpene by the raw material supplier to stabilize this ingredient with respect to oxidation prior to addition to the formulation.

The efficacy of the soft natural corn meal as a scrubber is enhanced in a low suds formula with high solvent power. Because of the gentle scrubbing action of the corn meal, the scrubbing action is more readily perceived in a low suds formula. Therefore, defoaming agents may form part of the present formulations in order to prevent excessive foaming. However, the heavy loading of organics in the formulations act in part as a defoaming agent.

Corn meal is an accepted scrubber in dry (anhydrous) hand cleansers but is problematic in typical skin cleansing formulations containing anionic or cationic surfactants due to reaction between these surfactants and the corn meal resulting is softening of the latter. The present invention has solved this problem by determining that corn meal is not attacked or softened in terpene based formulations when nonionic surfactants are used as the primary surfactant. Anionic and cationic surfactants are generally the primary surfactant in skin cleansing formulations to give foaming and detergency. The formulations disclosed herein are unique because they use nonionic surfactants as the primary surfactant system in which the corn meal is stable. The loss of foaming is advantageous because it enhances the scrubbing effect of the corn meal. However, the loss of detergency due to the lack of anionic or cationic surfactants is compensated for by the use of the terpene which enhances the detergency of the nonionic surfactants.

The efficacy of the present cleansing formulations toward hydrocarbon based soils was determined using test materials such as roofing asphalt, fifth wheel grease, various inks and the like.

Those skilled in the art will readily understand that many of the components of the formulation may serve more than one functional purpose. For example, the multi-functional ingredient PPG-24-Glycereth-24 aids emulsification of the d-limonene, provides solvency for inks and other soils, and acts as a defoaming agent to enhance the efficacy of the corn meal scrubber.

Various dyes may be included for ascetic purposes in the different cleansing formulations disclosed herein. For example, FD & C Yellow No. 5 is a yellow dye and FD & C Blue No. 1 is a blue dye with both dyes certified to comply with specifications published in the U.S. Code of Federal Regulations for Food, Drug and Cosmetic Colors.

Ranges For Cleansing Solution Formulations

Ranges in which the minimal number of required functional constituents comprising the skin cleaning formulations forming the present invention may vary are as follows.

| Ingredient | Min Weight % | Max Weight % |
|---|---|---|
| Water | 35 | 90 |
| Terpene | 0.9 | 40 |
| Corn Meal | 3 | 20 |
| Surfactant | 4 | 20 |
| Preservatives | 0.05 | 2.35 |

Ranges in which specific ingredients may be varied for a non-limiting formulations are given herebelow:

EXAMPLE #1

| Ingredient | Preferred Value | Min Weight % | Max Weight % |
|---|---|---|---|
| Water | 71.0 | 64.0 | 78.0 |
| Carbomer 934 | 0.4 | 0.3 | 0.6 |
| Citrus Terpenes | 1.0 | 0.9 | 1.1 |
| Corn Meal | 6.0 | 4.0 | 8.0 |
| Propylene Glycol | 4.0 | 3.0 | 5.0 |
| PEG-75 Lanolin | 2.0 | 1.5 | 3.0 |
| Cocamide DEA | 1.0 | 0.5 | 1.5 |
| Nonoxynol-10 | 7.5 | 6.0 | 9.0 |
| Nonoxynol-6 | 4.0 | 2.0 | 6.0 |
| Germaben II (TM*) | 0.50 | 0.25 | 0.75 |
| Sodium Hydroxide 20% | 0.54 | 0.40 | 0.80 |

To prepare formulations within these ranges the general procedure is to disperse the carbomer with cold water through an eductor into a clean vessel containing the remaining water heated to about 38 degrees Celsius. Add the propylene glycol, PEG-75 lanolin (melted), corn meal, Germaben II, cocamide DEA and mix thoroughly. Add the citrus terpenes, nonoxynol-10 and nonoxynol-6. When the formulation is uniform then neutralize with sodium hydroxide solution.

Sodium hydroxide is used to neutralize the acidic carbomer and the pH of the product containing the neutralized carbomer is in the range from about 5 to 8, but may be as high as 8.5 for some formulations. The acid forms of the carbomer generally do not swell until neutralized.

As a general rule, in preparing the various skin cleansing formulations of the present invention from within the above noted ranges, the preferred formulations are those in which the terpene level is chosen to give the desired solvency and then the surfactant composition and concentration is chosen to obtain adequate emulsification of the terpene in addition to providing suitable detergency. Stability of emulsions may be tested using known techniques such as freeze/thaw, accelerated aging by heat or any other method appropriate to the expected use of the formulation.

As many suitable preservatives are also surface active agents, it is advisable to confirm that the choice of preservative does not adversely affect the stability of the emulsion.

The skin cleansing formulations of the present invention will be further illustrated using the following non-limiting examples giving specific formulations.

EXAMPLE #1: LOTION SKIN CLEANSER

| INGREDIENT | % WT | PURPOSE |
|---|---|---|
| Water | 70.8 | |
| d-Limonene | 10.0 | |
| Corn Meal | 8.0 | Scrubber |
| Dodecyl Thioethoxylate | 7.5 | Nonionic surfactant |
| PPG-24-Glycereth-24 | 2.0 | Solubilizer |
| PEG-75 Lanolin | 0.4 | Solubilizer, emollient |
| Carbomer 940 | 0.3 | Polymeric thickener |
| Triethanolamine | 0.5 | Organic neutralizer |
| Preservatives | 0.5 | |

This lotion skin cleanser formulation was prepared by mixing into a clean vessel with adequate propeller type mixing the d-limonene, dodecyl thioethoxylate, PPG-24-glycereth-24, PEG-75 Lanolin, and oil soluble preservatives. In a separate clean vessel, the corn meal and Carbomer 940 were dry blended. With the mixer running, the dry blend of corn meal and Carbomer 940 was added to the d-limonene mixture. Water heated to 35–40 degrees Celsius and water soluble preservatives were added with mixing until uniform. Triethanolamine was then added to the mixture with paddle mixing until the formulation was uniform.

EXAMPLE #2: LOTION SKIN CLEANSER

| INGREDIENT | % WT | PURPOSE |
| --- | --- | --- |
| Water | 72.8 | |
| d-Limonene | 1.0 | |
| Corn Meal | 6.0 | Scrubber |
| Carbomer 934 | 0.35 | Polymeric thickener |
| Propylene Glycol | 5.0 | Solvent |
| PEG-75 Lanolin | 1.5 | Solubilizer, emollient |
| Cocamide DEA | 1.0 | Nonionic Surfactant |
| Nonoxynol-6 | 7.2 | Nonionic surfactant |
| Nonoxynol-9 | 4.8 | Nonionic surfactant |
| Sodium Hydroxide | 0.15 | Alkaline neutralizer |
| Preservatives | 0.2 | |

This lotion skin cleanser formulation was prepared using cold water to disperse the Carbomer 934 through an eductor. When dispersed, the dispersion was heated to 35–40 degrees Celsius and the propylene glycol, PEG-75 Lanolin and the corn meal were added with mixing. When the corn meal was dispersed the cocamide DEA and d-limonene were added. The preservatives, the nonoxynol-6 and nonoxynol-9 were then added with stirring. The sodium hydroxide was then added as a 20% solution in water and the resulting formulation mixed until uniform.

EXAMPLE #3: VISCOUS LOTION SKIN CLEANSER

| INGREDIENT | % WT | PURPOSE |
| --- | --- | --- |
| Water | 70.6 | |
| d-Limonene | 10.0 | |
| Corn Meal | 8.0 | Scrubber |
| Pareth-15-9 | 7.5 | Nonionic surfactant |
| Hexylene Glycol | 2.0 | Solubilizer |
| PEG-75 Lanolin | 0.2 | Solubilizer, emollient |
| Carbomer 940 | 0.4 | Polymeric thickener |
| Triethanolamine | 0.7 | Organic neutralizer |
| Preservatives | 0.5 | |

This viscous lotion was prepared by mixing into a clean vessel with adequate propeller type mixing the d-limonene, Pareth-15-9, hexylene glycol, PEG-75 Lanolin, and oil soluble preservatives. The Carbomer 940 and the corn meal were dry blended in a separate vessel. The dry blended Carbomer and corn meal were then added to the d-limonene solution with the mixing. The water was heated to 35–40 degrees Celsius and added along with the water soluble preservatives and paddle mixed until the mixture was uniform. The triethanolamine was then added and the resulting formulation mixed until uniform.

EXAMPLE #4

| INGREDIENTS | WT % | PURPOSE |
| --- | --- | --- |
| Water | 70.66 | |
| d-Limonene | 5.0 | |
| Corn Meal | 8.0 | Scrubber |
| Nonoxynol-10 | 11.25 | Nonionic surfactant |
| Hexylene Glycol | 2.0 | Solubilizer |
| PEG-75 Lanolin | 0.2 | Solubilizer, emollient |
| Carbomer 647 | 2.34 | Polymeric thickener |
| Preservatives | 0.55 | |

This skin cleansing formulation was prepared by mixing into a clean vessel, with adequate propeller type mixing, the nonoxynol-10, d-limonene, hexylene glycol, corn meal and oil soluble preservatives. Water was heated to 35–40 degrees Celsius to which the PEG-75 Lanolin and water soluble preservatives were added with mixing. The water solution was then added to the d-limonene mixture with mixing until uniform. The Carbomer 647 was added with paddle mixing until the formulation was thick and uniform.

EXAMPLE #5

| INGREDIENT | WT % | PURPOSE |
| --- | --- | --- |
| Water | 68.5 | |
| Citrus Terpenes | 7.5 | |
| Corn Meal | 8.0 | Scrubber |
| Nonoxynol-6 | 11.25 | Nonionic surfactant |
| Hexylene Glycol | 2.0 | Solubilizer |
| PEG-75 Lanolin | 0.2 | Solubilizer, emollient |
| Carbomer 647 | 2.0 | Polymeric thickener |
| Preservatives | 0.55 | |

This skin cleansing formulation was prepared by mixing into a clean vessel the nonoxynol-6, citrus terpenes, hexylene glycol, corn meal and any oil soluble preservatives. The mixture was mixed well. The water was heated to 35–40 degrees Celsius and the PEG-75 Lanolin and water soluble preservatives were added and the mixture was mixed until uniform. The water solution was added to the citrus terpene mixture and the resulting solution mixed until uniform. The Carbomer 647 was added and the resulting formulation paddle mixed until thick and uniform.

EXAMPLE #6: LOTION SKIN CLEANSER

| INGREDIENT | % WT | PURPOSE |
| --- | --- | --- |
| Water | 64.03 | |
| d-Limonene | 10.0 | |
| Corn Meal | 8.0 | Scrubber |
| Fatty Alcohol Ethoxylate-10 | 9.0 | Nonionic surfactant |
| Fatty Ethoxylate-6.5 | 4.0 | Nonionic surfactant |
| Cocamide DEA | 3.0 | Nonionic surfactant |
| Ethoxylated Lanolin | 0.2 | Solubilizer emollient |
| Carbomer 940 | 0.50 | Polymeric thickener |
| Sodium Hydroxide | 0.22 | Alkaline neutralizer |
| Wheatgerm Aqueous | 0.10 | Skin Conditioner |
| Preservatives | 0.05 | |

This skin cleansing formulation is prepared in the same manner as above example 2.

The flash point of d-limonene is about 48 degrees Celsius so that in order to reduce the risk of fire or explosion, the formulations of this ingredient should be prepared at temperatures below 48 degrees Celsius. In addition, the mixing vessels should be grounded to avoid static discharge.

While the skin cleansing formulations have been described and non-limiting examples given with respect to the various ingredients, it will be appreciated that numerous variations of these formulations may be made without departing from the scope of the invention as disclosed herein.

Therefore what is claimed is:

1. A cleansing formulation for application to the skin, comprising:

in combination, water, a physiologically acceptable terpene present in the range from about 0.9% to about 40% by weight, a nonionic surfactant present in the range from about 4% to 20% by weight, said nonionic surfactant being the primary surfactant in the formulation, corn meal scrubber present in the range from about 3% to about 20%, and a preservative present in the range from about 0.05% to about 2.35% by weight.

2. A cleansing formulation according to claim 1 wherein said physiologically acceptable terpene is derived from oranges.

3. A cleansing formulation according to claim 2 including a solubilizer selected from the group consisting of ethers of glycerin, ethoxylated tanolin and hexylene glycol, wherein said solubilizer is present in the range from about 0.20 to 3% by weight.

4. A cleansing formulation according to claim 2 including a thickening agent selected from the group consisting of polymers derived from cellulose gum, and cross-linked polymers and copolymers derived from acrylic acids.

5. A cleansing formulation according to claim 2 wherein said nonionic surfactant is selected from the group consisting of alkyl phenol ethoxylates, alcohol ethoxylates, amine oxides, amides, and combinations thereof.

6. A cleansing formulation according to claim 2 wherein said preservative is selected from the group consisting of anti-microbial agents and anti-oxidants.

7. A cleansing formulation according to claim 6 wherein said antimicrobial agents are selected from the group consisting of methylparaben, propylparaben, diazolidinyl urea, polymethoxy bicyclic oxazolidine, derivatives of para-hydroxybenzoic acid, formaldehyde, imadazolidinyl urea, phenoxyethanol, chloroxylenol, DMDM hydantoin, and blends of methylchloroisothiazolinone and methylisothiazolinone.

8. A cleansing formulation according to claim 6 wherein said anti-oxidant agents are selected from the group consisting of butylated hydroxytoluene, butylated hydroxyanisole, sodium sulfite and tocopherol.

9. A skin cleansing formulation according to claim 1 wherein said physiologically acceptable terpene is derived from citrus fruit.

10. A cleansing formulation according to claim 9 wherein said preservative is selected from the group consisting of anti-microbial agents and anti-oxidant agents.

11. A cleansing formulation according to claim 10 wherein said antimicrobial agents are selected from the group consisting of methylparaben, propylparaben, diazolidinyl urea, polymethoxy bicyclic oxazolidine, derivatives of para-hydroxybenzoic acid, formaldehyde, imadazolidinyl urea, phenoxyethanol, chloroxylenol, DMDM hydantoin, and blends of methylchloroisothiazolinone and methylisothiazolinone.

12. A cleansing formulation according to claim 10 wherein said antioxidant agents are selected from the group consisting of butylated hydroxytoluene, butylated hydroxyanisole, sodium sulfite and tocopherol.

13. A cleansing formulation for application to the skin, comprising;

a) water;

b) a terpene derived from oranges present in the range from about 0.9% to 40% by weight;

c) corn meal scrubber present in the range from about 3% to about 20% by weight;

d) nonionic surfactants present in the range from about 4% to about 20% by weight and which nonionic surfactants are the primary surfactants in the formulation;

e) a preservative comprising an antimicrobial agent and an antioxidant agent, said preservative being present in the range from about 0.05% to about 1.3% by weight; and f) a thickening agent present in the range from about 0.30% to about 2.35% by weight.

14. A cleansing formulation according to claim 13 including a solubilizer present in the range from about 0.20 to 3% by weight.

15. A cleansing formulation according to claim 14 wherein said solubilizer is selected from the group consisting of ethers of glycerin, ethoxylated lanolin and hexylene glycol.

16. A cleansing formulation according to claim 15 wherein said ethers of glycerin are selected from the group consisting of PPG-24-Glycereth-24, PPG-66-Glycereth-12 and PPG-20-Glycereth-30.

17. A low sudsing cleansing formulation for application to the skin, comprising:

a thickened stable emulsion including water, a physiologically acceptable terpene present in the range from about 0.9% to about 40% by weight, a nonionic surfactant present in the range from about 4% to 20% by weight and wherein said nonionic surfactant is the primary surfactant in the formulation, a corn meal scrubber present in the range from about 3% to about 20%, and a preservative agent present in the range from about 0.05% to about 2.35% by weight, said terpene, said nonionic surfactant, said corn meal scrubber and said preservative agent being combined with said water so that the viscosity of said emulsion remains stable and said corn meal scrubber does not soften.

18. A low sudsing thickened cleansing emulsion formulation for application to the skin, comprising;

a) water;

b) a terpene present in the range from about 0.9% to 40% by weight;

c) corn meal scrubber present in the range from about 3% to about 20% by weight;

d) nonionic surfactants present in the range from about 4% to about 20% by weight and wherein said nonionic surfactants are the primary surfactants in the formulation;

e) a preservative comprising an antimicrobial agent and an antioxidant agent, said preservative being present in the range from about 0.05% to about 1.3% by weight;

f) a thickening agent present in the range from about 0.30% to about 2.35% by weight; and g) said terpene, said nonionic surfactant, said thickening agent, said corn meal scrubber and said preservative being combined with said water so that the viscosity of the emulsion remains stable and said corn meal scrubber does not soften.

* * * * *